(12) United States Patent
Homutov et al.

(10) Patent No.: US 9,757,559 B2
(45) Date of Patent: Sep. 12, 2017

(54) ELECTRET IMPLANT FOR TREATMENT OF ARTHROSIS

(71) Applicant: LIMITED LIABILITY COMPANY "MEDEL", St. Petersburg (RU)

(72) Inventors: Victor Pavlovich Homutov, St. Petersburg (RU); Mikhail Samuilovich Morgunov, St. Petersburg (RU)

(73) Assignee: "MEDEL", LLC, St. Petersburg (RU)

( * ) Notice: Subject to any disclaimer, the term of this patent is extended or adjusted under 35 U.S.C. 154(b) by 0 days.

(21) Appl. No.: 15/034,220

(22) PCT Filed: Jul. 11, 2014

(86) PCT No.: PCT/RU2014/000511
§ 371 (c)(1),
(2) Date: May 4, 2016

(87) PCT Pub. No.: WO2015/076698
PCT Pub. Date: May 28, 2015

(65) Prior Publication Data
US 2016/0367798 A1    Dec. 22, 2016

(30) Foreign Application Priority Data

Nov. 21, 2013    (RU) ................................ 2013151988

(51) Int. Cl.
*A61N 1/10*        (2006.01)
*A61L 27/50*       (2006.01)
(Continued)

(52) U.S. Cl.
CPC ................ *A61N 1/10* (2013.01); *A61L 27/34* (2013.01); *A61L 27/50* (2013.01); *A61L 31/088* (2013.01);
(Continued)

(58) Field of Classification Search
None
See application file for complete search history.

(56) References Cited

U.S. PATENT DOCUMENTS 3,968,790 A    7/1976  Fukada et al.
5,759,205 A *  6/1998  Valentini ............. A61L 33/0094
                                                    433/173
(Continued)

FOREIGN PATENT DOCUMENTS

WO            95/19796 A1    7/1995

OTHER PUBLICATIONS

International Search Report of May 12, 2016.
International Search Report of Nov. 17, 2014.

*Primary Examiner* — Ankit D Tejani
(74) *Attorney, Agent, or Firm* — Arent Fox LLP; Michael Fainberg

(57) ABSTRACT

The invention relates to electret implant and to electrotherapy using static electricity of electret coatings for treatment of arthrosis of different joints: knee, hip, and shoulder, including for the arthrosis treatment of small bones of arms and legs. The inventive electret implant includes an extended body with a proximal and a distal end. On surface of the body a dielectric coating in an electret state is formed. The implant, wherein its body is implemented as a rod, at the proximal end of which a frontal surface is formed, and the fixation device of the implant in the hole in the bone can be made at the distal end. The bushing, wherein on its outer surface a thread for its set is made in the hole in the bone, and on its inner surface a thread for fixation of the electret implant in the hole is made.

18 Claims, 5 Drawing Sheets

(51) Int. Cl.
*A61N 1/20* (2006.01)
*A61L 27/34* (2006.01)
*C08L 27/18* (2006.01)
*A61L 31/08* (2006.01)
*A61L 31/10* (2006.01)
*A61L 31/14* (2006.01)
*A61N 1/32* (2006.01)

(52) U.S. Cl.
CPC ............... *A61L 31/10* (2013.01); *A61L 31/14* (2013.01); *A61N 1/205* (2013.01); *C08L 27/18* (2013.01); *A61L 2400/00* (2013.01); *A61L 2430/02* (2013.01); *A61N 1/326* (2013.01)

(56) References Cited

U.S. PATENT DOCUMENTS

| | | | |
|---|---|---|---|
| 8,145,319 B1 | 3/2012 | Simon | |
| 2005/0059972 A1 | 3/2005 | Biscup | |
| 2006/0190080 A1 | 8/2006 | Danoff | |
| 2009/0048675 A1* | 2/2009 | Bhatnagar | A61B 17/0642 623/17.16 |
| 2010/0204736 A1* | 8/2010 | Biedermann | A61B 17/7008 606/264 |
| 2010/0318140 A1* | 12/2010 | Hintz | A61N 1/378 607/5 |
| 2013/0053890 A1* | 2/2013 | Elshihabi | A61B 17/701 606/261 |

* cited by examiner

ELECTRET IMPLANT FOR TREATMENT OF ARTHROSIS

TECHNICAL FIELD

The invention relates to the field of medicine, and more particularly, to an electret implant.

BACKGROUND OF THE INVENTION

Since the 80s a new branch of medicine based on the use of short-range static electric fields to stimulate positive biological processes in the human body has formed and rapidly developed. The main distinguishing feature of practical methods that are based on this concept is that electric fields are not made by traditional electrical power sources with network or battery power, it is made by autonomously functioning electret films.

Electret is a dielectric on the surface or in the bulk of which non-compensated electric charges are preserved for a long time. These charges produce an electric field in the space surrounding an electret. Getting together with an implant to the human body, an electret film by its field has a local effect on the damaged organ, contributing to its treatment. The electric field of certain magnitude and sign, acting at the cellular level, is the catalyst of reparative processes in living tissues.

US 2005/0059972 A1 discloses a pedical screw including a head and a lower portion wherein to the head is connected a head-piece, wherein different head-pieces can be connected to the pedical screw. The lower portion of the pedical screw includes a thread for anchoring the pedical screw in a bone.

Similarly, US 2009/0048675 A1 represents a general prior art for the present invention, disclosing a bone fusion device, comprising a body portion, a first inserting portion extending from the body portion for engaging a first bone, and a second inserting portion extending from the body portion for engaging a second bone.

A method for treatment arthrosis of the femoral head is known (see U.S. Pat. No. 8,145,319). Through the necrotic area of the femoral head an electric current is passed which stimulates the growth of bone tissue in the femoral head affected by arthrosis.

To carry out this method a device for electrostimulation of the bone tissue growth is used (see U.S. Pat. No. 8,145,319). The device includes a cathode and an anode remote from each other and connected with the battery by wires, and a control unit. The control unit and the battery are placed in an electrically conductive housing, which acts as the anode.

To begin the process of electrostimulation, you must first place the cathode in its permanent workplace. To do this it is necessary to perform a decompression dead hole in the femoral head affected by arthrosis. An axis of the hole is directed to an area of maximum lesion by necrosis. Then, the cathode is placed in this hole, using a dowel of a resorbable polymer. The cathode made of bare titanium wire is tightened by the dowel to the bottom of the decompression dead hole in order to ensure maximum electrical contact of the cathode with the necrotic area of a bone. The second function which is provided by the dowel is to hold the cathode in the hole in its place, ensuring conservation of the largest cathode contact with the walls and the bottom of the decompression hole. For this purpose, the dowel is placed into the decompression hole without a gap, i.e. closely. Later the dowel resolves and the cathode grows into the bone of the femoral head forever. An electricity wire comes out to the body surface from the bone. The electric current is supplied through the electricity wire to the battery.

After placement of the cathode by the pin in its place in the hole it is possible to begin to conduct electrical stimulation of the growth of healthy bone tissue. For this purpose the battery potential difference is supplied to the cathode and anode. Then, the anode is pressed against the patient's skin. A catenation closure occurs at that. The electric current starts to flow between the cathode and the anode through the body tissue of the patient, stimulating the growth of bone tissue of the femoral head. Because the decompression hole can be directed exactly to the area of maximum lesion by necrosis and it may be of any desired depth, the cathode can be placed in the optimal point of space of the femoral head, i.e. in the immediate vicinity of the zone of necrotic lesion that ensures the highest possible therapeutic effect on bone tissue.

A disadvantage of the method-analogue is that the electric current flowing from the cathode to the anode passes through tissues: skin, periosteum, fatty tissues and others. This leads to a loss of the battery energy and hence it requires recharging.

Also, the electricity wire coming out of the bone from the cathode passes through the skin of the patient outside and is a source of constant infection.

In addition, the therapeutic effect of the device requires a constant fixation of the housing-anode to the human body, creating a lot of discomfort in everyday life.

Furthermore, during the therapeutic effect process of the device the introduction of charged ions of the anode metal material leads to the poisoning of body tissues through which the current flows.

Another method for treatment of arthrosis is known. The method includes the periodic application (twice a day for 1 hour) of a paper plate on the skin surface of the joint affected by arthrosis. A dielectric coating in an electret state is formed on the surface of the paper plate (see http://www.uralargo.ru/article/489, http://precission.ru/?id-_page=859373 and http://elis-deta.ru/elpast.html).

The disadvantage of this method for treatment of arthrosis is the distance of the electrostatic field generated by the electret coating from the joint lesion, which reduces the efficiency of this method-analogue, extending the treatment duration.

In addition, the periodicity of exposure to the lesion reduces the therapeutic effect duration of the electrostatic field of the electret coating, which also extends the treatment duration. Furthermore, when placing the plate on the surface of the movable joint, a mashing of a dielectric layer occurs, this leads to a loss of electret charge in it and makes the plate-analogue unsuitable.

These drawbacks are eliminated in the closest analogue.

Authors have chosen as the closest method-analogue a method for treatment of congenital hip joint malformation (see the USSR certificate of authorship No. 1,251,915), in which the femoral head occupies the wrong position relative to the pelvis, which leads eventually to the emergence of aseptic necrosis and degeneration of the head. During the treatment a portion of the femur is dissected (osteotomy), after that the femoral head is fixed in the correct position relative to the pelvis with the help of an electret implant.

The closest analogue is the electret implant according to the USSR certificate of authorship No. 1,251,915. The electret implant includes an extended body with a proximal and a distal end. The dielectric coating in an electret state is formed on its surface. Wherein the implant body is made as a plate. The proximal end is bent and is wedge-shaped, and two reach-through holes are made for screws at the distal end of the plate.

The closest method-analogue is implemented as follows: in the process of osteosynthesis the wedge-shaped end of the plate is hammered into the femoral head, and the distal end of the plate is tied to the second part of the femur, providing osteosynthesis. The electret potential along the plate distributes unevenly and has a maximum value in the osteotomy area (the bone dissection area) and in the wedge-shaped end of the plate.

Because the wedge-shaped end is placed into the pathological head, it is close to the bone pathology area. The electrostatic field generated by the electret coating having a maximum value at the wedge-shaped end, is as close as possible to the area of the necrotic lesion of the femoral head. This provides an increased electrostimulation of bone structures (compared to the previous analogue), leading to acceleration of the bone healing in the osteotomy area and prevention of development of destructive and degenerative processes in the femoral head.

Another disadvantage of the closest method-analogue is a violation of the electret coating integrity. Hammering of the wedge-shaped end into the femoral head is accompanied by friction of the electret coating on hard sharp chips. These chips are generated during hammering of the wedge-shaped end into the bone. During this process the violation of the electret coating integrity occurs in the wedge-shaped end zone, where a maximum electrostatic charge is concentrated. The violation of the electret coating integrity leads to a rapid discharge of the electret coating in the wedge-shaped end zone and weakening of the therapeutic action of the electrostatic field (until the complete action cessation) in the bone area where there is a maximum lesion of bone structures of the joint by the pathology.

The main purpose of the implant-analogue is osteosynthesis, i.e. a hard fixation of the femoral head relative to the dissected part of the femur during the treatment of the congenital disease associated with the wrong position of the head relative to the pelvis. The main thing that the electrostatic field of the electret coating works here on is osteosynthesis, i.e. stimulation of an accretion of parts of the dissected femur in the right mutual position relative to each other. The wedge-shaped proximal end serves here as a fastening element of a temporary design to the point when parts of the femur grow together and are able to perceive all loads of support-motor apparatus by yourself. Then the implant is removed from the bone because of its uselessness.

Thus, the main purpose of the electret coating on the implant surface is the optimization of osteosynthesis. The therapeutic effect of the electret coating electrostatic field on the surface of the wedge-shaped end gives an additional effect—an electrical stimulation of bone tissue inside the hip joint. It takes place during the accretion of dissected parts of the femur. After the implant removal the therapeutic effect of the electret coating electrostatic field on the joint pathology stops and pathological processes may be resumed.

Furthermore, the location of the electret implant toward the lesion of pathological destruction in the bone may not always be optimally chosen because the basic priority in choosing the direction of hammering of the wedge-shaped end of the implant into the bone is a high accuracy of the mutual position of connected parts of the bone (osteosynthesis). The optimization of osteoreparation is in second place, which reduces the efficiency of the therapeutic action of the electrostatic field on the pathological lesion in the bone.

Also, hammering of the wedge-shaped end increases the intraosseous pressure and requires drilling of several decompression holes in the bone (near the wedge-shaped end) to decrease the bone pressure. It further traumatizes the bone.

One more disadvantage of the electret implant which is the closest analogue is the magnitude of the total electrostatic charge on the wedge-shaped end of the implant. This is due to the fact that the proximal end of the implant is wedge-shaped, starting from a method of its application—hammering into the bone. On the edge of the wedge-shaped end, having a very small area, there is a proportionally small number of charges that proportionally reduces its impact on the effectiveness of reparative processes.

Another disadvantage of the implant-closest analogue is a dimensional limit for its placing in small-sized bones of arms and legs.

Also, implementation of the implant as the plate requires a large wrenching force to remove it from the hole in the case when the implant needs to be replaced.

Challenge arising from the prior art is a creation of a new treatment method, preventing the violation of an electret coating integrity during the implant placing into the bone.

SUMMARY OF THE INVENTION

The subject-matter of the invention is an electret implant for treatment of arthrosis.

The task in the present method for treatment of arthrosis is solved by the fact that the electret implant placing into the bone is made during the treatment course. The method is characterized by a preliminary performed hole in the bone directed towards a zone of maximum lesion by pathological process. The electret implant is placed with a gap into the prepared hole in the bone so that it is as close as possible to the bone area affected by the pathological process. To prevent a displacement of the implant from the optimal position for treatment the hole in the bone the implant is set by a fixation device. After fixing it in the hole the electret implant is left in the patient's bone to the moment when a pain syndrome appears once again, which is associated with the fact that the electret is discharged and no longer has a stimulating effect on bone structures.

Because the hole directed to the area of maximum destruction by the pathological process was preliminary made in the bone, the electret implant is placed with a gap in this hole so that it is as close as possible to the bone area affected by the pathological process. The electret coating surface of the proximal end of the electret is not damaged, namely the proximal end has the maximum charge magnitude, and thus has the maximum therapeutic effect on bone tissues. Thus, the implementation of the preliminary hole and the implant placement into it with a gap contributes to the electret coating charge conservation, allows conservation of the electrostatic charge magnitude and stability, lengthening of the therapeutic action duration of the electrostatic field on damaged bone tissues by the pathological process in comparison with the closest analogue. In this analogue the wedge-shaped proximal end is hammered into the bone, leading to the violation of the electret coating integrity in the wedge-shaped end area, the rapid discharge of the electret coating, and consequently, the reduction of the therapeutic action duration of the electrostatic field on bone tissues.

Furthermore, in the inventive method we are able to accurately orient the implant relative to bone tissue affected by the pathology, optimizing the healing process and increasing its effectiveness in comparison with the closest analogue. In it the direction of hammering of the wedge-shaped end into the bone is selected primarily basing on the need of an accurate mutual orientation of bone parts connected by the implant (osteosynthesis).

Furthermore, thanks to the fact that the implant is placed into the hole in the bone with a gap it allows to remove the excess tension inside the bone, get rid of additional decompression holes (as it occurs in the nearest method-analogue, wherein the implant is hammered into the bone), which makes the inventive method easier and reduces traumatism of its effects on the bone.

When the electret coating discharges, the discharged implant is removed from the bone and the new one is placed instead of the old one. The new one is a charged implant which resumes its therapeutic effect on bone tissues.

As a fixation device of the electret implant in the hole in the bone a bushing can be used. It is placed in the hole in the bone coaxially to this hole. Through the bushing the implant can be placed inside the hole in the bone and removed therefrom.

The bushing can be placed in the hole in the bone aflush with the outer surface of the bone.

The task of the inventive electret implant, arising from the prior art, is to ensure implementation of the method for treatment of arthrosis.

Another object of the inventive electret implant is to increase the total electrostatic charge at the proximal end of the implant.

Furthermore, the inventive electret implant solves the problem of the hole diameter reduction required for placing the implant into the hole in the bone with a gap.

In addition, the inventive electret implant solves another problem: reduction of efforts for wrenching the implant and reduction of bone traumatism in case of the implant replacement.

Problems are solved due to the fact that the inventive electret implant includes an extended body with a proximal and a distal end. On surface of the body a dielectric coating in an electret state is formed. The distinguishing feature of this implant is that its body is implemented as a rod, at the proximal end of which a frontal surface is formed, and a fixation device of the implant in a hole in a bone can be made at the distal end.

Due to the fact that the implant is made in the form of a rod, and the frontal surface is formed at the proximal end, there is an increase of the coating surface area of the proximal end in comparison with the closest analogue, in which the proximal end is wedge-shaped. Consequently, we obtain the much larger total charge at the proximal end of the proposed implant in comparison with the total charge at the wedge-shaped proximal end of the closest analogue and we increase the total area of contact of the implant with the bone. Thus, the therapeutic effect of the inventive implant on the zone affected by necrosis is significantly stronger than the effect of the electret coating with the wedge-shaped proximal end of the closest analogue. Accordingly, the therapeutic efficiency of the proposed implant is much higher than that for the closest analogue.

A spherical radius of the frontal surface edge of the implant proximal end can preferably be in the range from 0.1 mm to 3 mm.

The rod may be made of metal.

The rod may also be made of non-metal. Wherein an electrically conductive layer between the rod and the dielectric coating needs to be formed. It allows the charging possibility of the dielectric coating.

As the insulating coating of the rod polytetrafluoroethylene, and (or) its copolymers, and any other polymers and its compositions, which are dielectrics and have electret properties, may be used.

As the insulating coating of the rod tantalum pentoxide or other oxides of valve metals can be used.

The rod may have circular section in a plane perpendicular to its axis. For the manufacturing of the rod also other cross-sectional shapes close to a circular cross-section can be used.

The device for the implant fixation in the hole in the bone can be formed by the fact that the distal end of the rod is bent at an angle to the rod axis, and therein a reach-through hole for a screw for bonding to the bone is made.

The device for the implant fixation can be formed by the fact that a head with a conical outer surface for bonding with the bone is formed at the distal end, and at least one screwdriver slot is made on the frontal surface of the head.

The device for the implant fixation can be formed by the fact that the head with a thread on its lateral surface is formed at the distal end of the rod, and at least one screwdriver slot is made on the frontal surface of the head.

The device for the implant fixation can be formed by the fact that the distal end of the rod is pointed and is bent twice at right angle so that pointed distal end is directed in parallel with the axis of the rod toward the proximal end.

The reach-through hole to extract the rod from the hole in the bone, when replacing the discharged electret implant by the new one with the charged dielectric coating, can be formed at the distal end of the rod.

The device for the implant fixation can be formed as a cylindrical bushing, and on its outer surface a thread for its set in the hole in the bone is made, and on its inner surface a thread for fixation of the electret implant in the hole is made. At least one screwdriver slot is made on the frontal surface of the bushing. The bushing also provides for placing and removal of the implant in the hole in the bone.

DESCRIPTION OF PREFERRED EMBODIMENTS

Let's consider the embodiment of the inventive method by the example of treatment of dysplastic coxarthrosis of the left femoral head.

Figure 1:
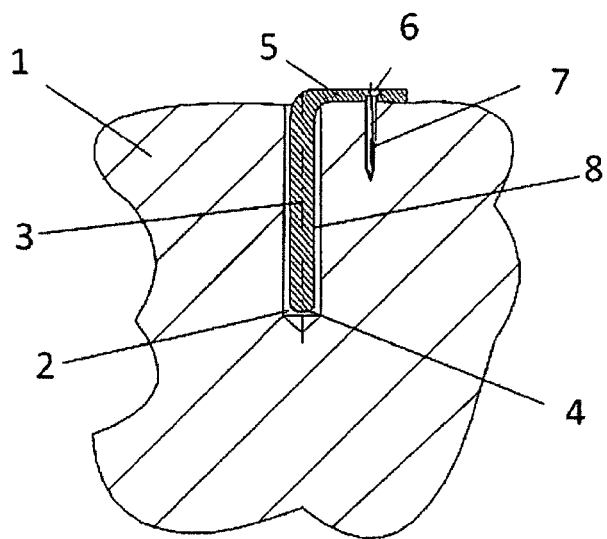
FIG. 1 is a side view of an electret implant placed in a hole in a bone and fixed in the bone by a screw.
Figure 2:
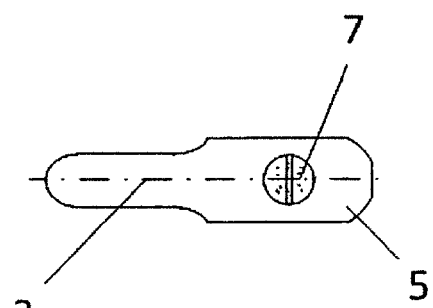
FIG. 2 is a top view of an electret implant placed in a hole in a bone and fixed in the bone by a screw.

Patient K. (born in 1954) was admitted to the traumatology and orthopedics clinic of the Kirov Military Medical Academy on occasion of the above-mentioned diagnosis on 8 Apr. 1996 (case history No. 8276). The patient was treated according to the inventive method: during the surgery under the local anesthesia a cylindrical hole 2 with a diameter of 4.2 mm was made in the patient's bone 1 (FIG. 1, FIG. 2). An electret implant in the form of a cylindrical rod 3 with a diameter of 4 mm was placed in the hole 2. The rod 3 had a rounded proximal end 4 and a distal end 5 bent at an angle to the axis of the rod 3. At the proximal end 4 of the rod 3 a frontal surface is formed with rounded edge. At the bent end 5 a reach-through hole 6 was made. Through that hole 6 a screw 7 was twisted into the bone 1 for fixation of the rod 3 relative to the bone 1. The rod 3 is made of tantalum. On its surface a dielectric coating 8 of tantalum pentoxide with a thickness of 0.3 microns was formed by anodic oxidation. That coating had a distribution of the electret potential with a maximum value at the proximal end 4 along the axis of the rod 3. The electret coating 8, being inside the bone 1 for a long time (5 years or more), had the therapeutic (restorative) effect on bone tissue 1, vessels, nerves and ligaments, etc., restoring the normal functioning of the joint. Two days after the introduction of the electret implant into the femoral head the pain stopped. Seven days later the patient was discharged from the hospital. After 7 years the patient underwent the repeated surgery to replace the implant 3 with the discharged electret coating 8 by the new implant 3 with the charged dielectric coating 8 in the 3rd city hospital of Saint-Petersburg (case history No. 22056). From 1996 to 2007 the bone tissue structure reconstruction of femoral head was marked, the patient completely refused medicaments, sanatorium-and-spa treatment was provided annually. A contact is maintained with the patient K. Until 2014 the pain in hip joints has not been renewed. Thus, the electret implant use has allowed avoiding total joint replacement.

Due to the fact that the implant is made in the form of a rod 3, and the frontal surface is formed at the proximal end 4, there is an increase of the coating surface area 8 of the proximal end 4 in comparison with the closest analogue, in which the proximal end is wedge-shaped. Consequently, we obtain the much larger total charge at the proximal end 4 of the proposed implant 3 in comparison with the total charge at the wedge-shaped proximal end of the closest analogue and we increase the total area of contact of the implant 3 with the bone 1. Thus, the therapeutic effect of the inventive implant 3 on the zone affected by necrosis is significantly stronger than the effect of the electret coating 8 with the wedge-shaped proximal end of the closest analogue. Accordingly, the therapeutic efficiency of the implant 3 is significantly higher than that for the closest analogue.

Because the implant 3 is placed into the hole 2 with a gap, the surface of the dielectric coating 8 is not damaged and it contributes to the charge conservation of the electret coating 8, increasing the coating area, acting on the affected bone structure, and lengthening (more than 5 years) the therapeutic action duration of the electrostatic field on damaged bone tissues by the pathological process in comparison with the closest analogue. In this analogue the wedge-shaped proximal end is hammered into the bone, leading to the violation of the electret coating integrity in the wedge-shaped end area, the electrostatic charge loss, the rapid discharge of the electret coating, and consequently, the reduction of the therapeutic action duration of the electrostatic field on bone tissues.

The above-described inventive treatment method is one of the possible embodiments of the proposed method of treatment and uses one of the possible embodiments of the implant 3 and one of the possible embodiments of the fixation device of the implant 3 in the hole 2.

Figure 3:
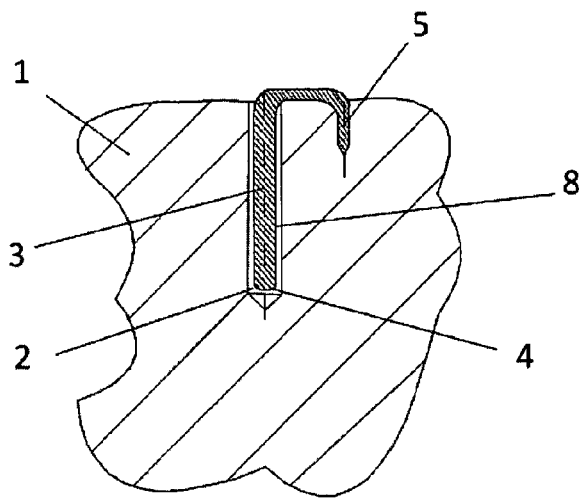
FIG. 3 is a side view of an electret implant with a bent distal end placed in a hole in a bone and fixed in the bone by a pointed distal end.

The implant 3 may be placed in the hole 2 (see FIG. 3) and fixed in the bone 1 by a pointed distal end 5. Thus the electret coating 8 of a proximal end 4 does not contact with the bone 1 during the placing process and its integrity is not damaged.

Figure 4:
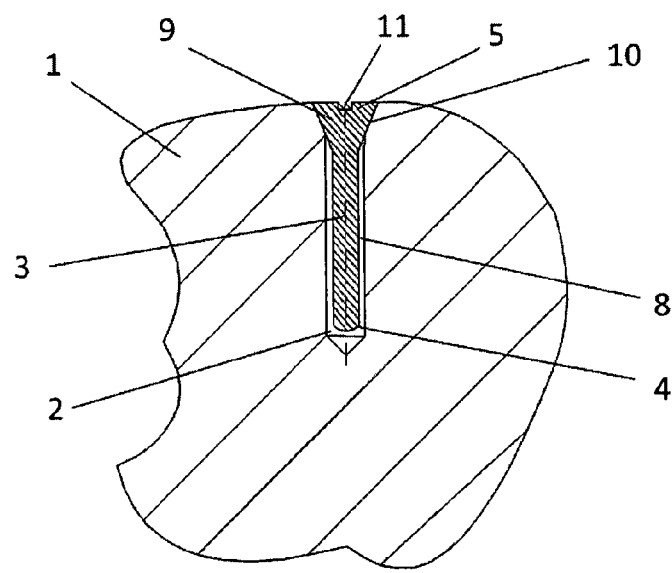
FIG. 4 is a side view of an electret placed in a hole in a bone and fixed by a head with a conical outer surface for bonding with the bone.

The implant 3 may also be placed into the hole 2 (see FIG. 4) and fixed tightly in the bone 1 by a head 9 with a conical outer surface 10. On the frontal surface of the head 9 a screwdriver slot 12 is made.

Figure 5:
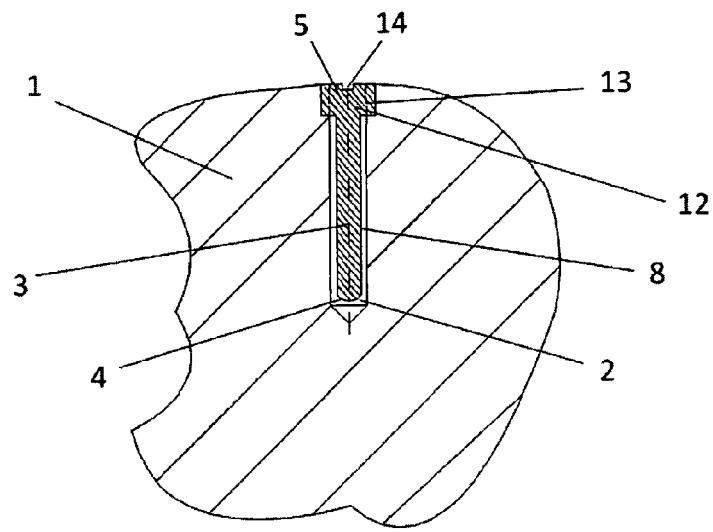
FIG. 5 is a side view of an electret placed in a hole in a bone and fixed by a thread formed on a cylindrical head of a rod.

The implant 3 may also be placed into the hole 2 (see FIG. 5) and fixed into the bone 1 by a cylindrical head 12, on the lateral surface of which a thread 13 is made. The implant 3 is twisted into the bone 1 by a screwdriver inserted into a slot 14. The implant 3 is removed from the bone 1 by unscrewing it from the bone 1.

Figure 6:
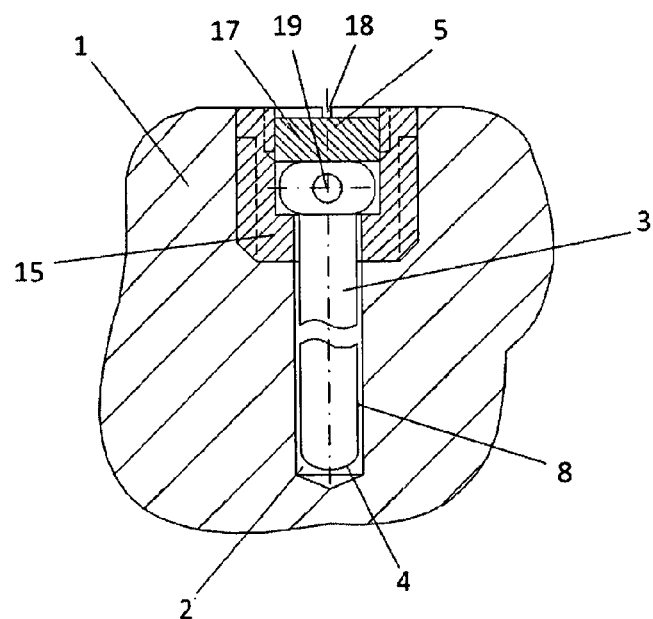
FIG. 6 is a side view of an electret implant placed in a hole in a bone through a bushing and fixed by a cap.
Figure 7:
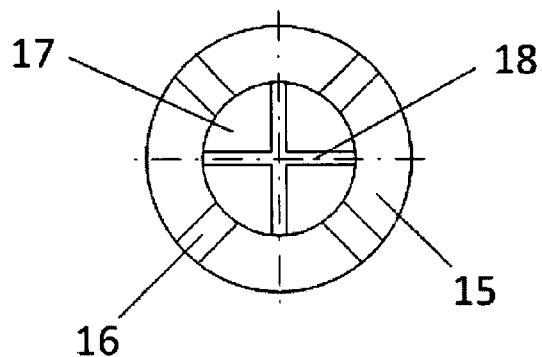
FIG. 7 is a top view of an electret implant placed in a hole in a bone through a bushing and fixed by a cap.
Figure 8:
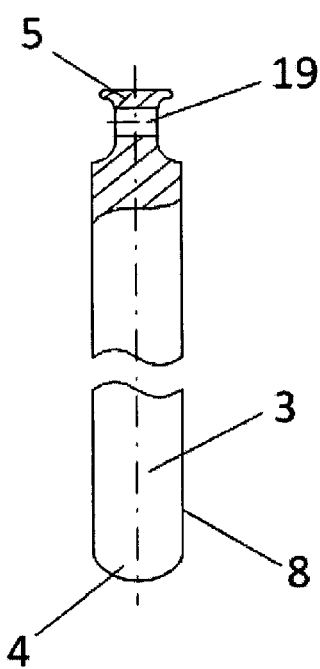
FIG. 8 shows a 90-degree displacement of the electret implant of FIG. 7 with a hole for removal it from the bone.

The implant 3 may also be placed into the hole 2 and fixed into the bone 1 by a cylindrical bushing 15 (see FIG. 6, 7, 8) screwed into the bone 1 by a screwdriver coaxially to the hole 2 and inserted into a slot 16.

A screw cap 17 is used to fix the implant 3 into the hole 2. The screw cap is twisted into the bushing 15 by a screwdriver slot 18, closing the hole 2 in which the implant 3 is placed. To remove the waste (discharged) implant 3 the screw cap 17 is untwisted, the implant 3 is picked up for a hole 19 and is removed from the hole 2 in the bone 1. After that the charged implant 3 is placed into the hole 2 through the bushing 15. Then the implant 3 is fixed into the hole 2 by the screw cap 17 screwed into the bushing 15.

Figure 9:
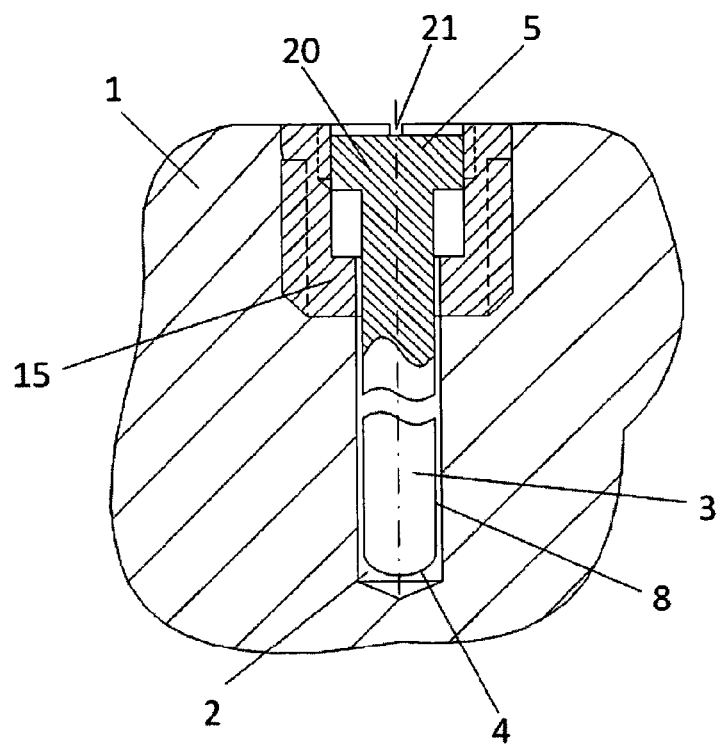
FIG. 9 is a top view of an electret implant placed in a hole in a bone through a bushing and fixed by a thread formed on a cylindrical head of a rod wrapped inside the bushing.

The implant 3 may also be placed and fixed into the hole 2 due to the fact that the implant 3 is screwed into the bushing 15 using a cylindrical head 20 (FIG. 9) which is screwed into the bushing 15 by a screwdriver through a slot 21.

Example No. 2. Patient of 58 years old was admitted to the 3rd city hospital of Saint-Petersburg with the diagnosis: inveterate damage of internal meniscus of anterior cruciate ligament and deforming arthrosis of the right knee. Medical diagnostic arthroscopy and meniscectomy were performed; the electret implant 3 was placed into the epiphysis of the tibia 1 on 27 Nov. 2009. Control radiography in the post-operative period (after 6, 12 and 24 months) showed no progression of the degenerative process in condyles of the tibia and the femur 1. The pain syndrome was arrested, the patient refused the course of analgesic drugs.

Example No. 3. Patient N. of 18 years old was admitted to the 3rd city hospital of Saint-Petersburg with the diagnosis of polyarthritis of unknown etiology. She was able to move only in a wheelchair. In April 1990, she underwent the surgery for the introduction of 3 tantalic electret implants in the hip and the knee joints. As a result a few days after the surgery the pain in joints stopped. After 7 days the patient was already able to move on her own feet. 12 days later she left the hospital and returned to normal life.

Example No. 4. In May 1991 the patient N. of 60 years old was admitted to the 3rd city hospital of Saint-Petersburg. The patient was exposed to harmful and toxic chemicals in his workplace. As a result his femoral heads began to disperse on the background of the lesion of blood and other structural and functional disorders in the body that were not allowed to use endoprosthesis replacement. The patient was bedridden. The surgery was carried out for the introduction of tantalum implants 3 into the affected joint bones 1. A week after the surgery the partial restoration of the joint function was fixed. Three weeks later, the patient began to walk. Of course, at first he walked with difficulty.

INDUSTRIAL APPLICABILITY

The inventive method was widely clinically tested in the Kirov Military Medical Academy, the 3rd city hospital of Saint-Petersburg, and children's orthopedic sanatorium of the USSR Ministry of Defense in Yevpatoria and showed a high efficiency.

More than 100 patients were operated and the disease was stopped in 97% of cases. It is not simply the removal of pain; it prevents the further development of the disease.

The total cost of the disease treatment is reduced by more than 10 times in comparison with endoprosthesis replacement. The need of postoperative rehabilitation is also eliminated.

The invention claimed is:

1. An electret implant for treating arthrosis, comprising:
    an extended body having a proximal end and a distal end;
    a dielectric coating in an electret state being formed on the proximal end of a surface of said body,
    a device for implant fixation in a bone,
    wherein said body of said implant is made in the form of a rod, at the proximal end of which a frontal surface is formed,
    wherein the device for the implant fixation is made at the distal end of said body and is adapted for fixation of the implant in a hole in said bone by its distal end only, without contact of the proximal end of the rod with the bone, wherein the implant is adapted to be removable, wherein the implant is placed with a gap into the hole in said bone.

2. The electret implant of claim 1, wherein a spherical radius of an edge of said frontal surface of said proximal end is in the range from 0.1 mm to 3 mm.

3. The electret implant of claim 1, wherein said rod is made of metal.

4. The electret implant of claim 1, wherein said rod is made of non-metal, and wherein an electrically conductive layer is formed between the rod and the dielectric coating.

5. The electret implant of claim 1, wherein polytetrafluoroethylene and/or its copolymers or all other polymers and its compositions with dielectric properties are used as the dielectric coating of said rod.

6. The electret implant of claim 1, wherein tantalum pentoxide or oxides of other valve metals with electret properties are used as said dielectric coating of said rod.

7. The electret implant of claim 1, wherein said rod has a circular cross-section in a plane perpendicular to its axis.

8. The electret implant of claim 1, wherein the device for the implant fixation is formed by a bent distal end of said rod at an angle to the axis of said rod, wherein a reach-through hole is provided at the bent distal end for a screw for bonding to said bone.

9. The electret implant of claim 1, wherein the device for the implant fixation is formed by a head with a conical outer surface for bonding with said bone at said distal end, wherein at least one screwdriver slot is provided on a frontal surface of said head.

10. The electret implant of claim 1, wherein the device for the implant fixation is formed by a cylindrical head with a thread on its lateral surface, wherein at least one screwdriver slot is provided on the frontal surface of said cylindrical head.

11. The electret implant of claim 1, wherein the device for the implant fixation is formed by said distal end of said rod being pointed and bent twice at right angle so that this pointed distal end is directed in parallel with an axis of said rod toward said proximal end.

12. The electret implant of claim 1, wherein a reach-through hole is provided at said distal end of said rod to extract said rod from the hole in said bone when replacing a discharged electret implant by a new one with a charged dielectric coating.

13. The electret implant of claim 1, wherein the device for the implant fixation is a bushing, wherein on its outer surface a thread for its set is made in said hole in said bone, and on its inner surface a thread for fixation of the electret implant in said hole is made, and wherein at least one screwdriver slot is made on a frontal surface of said bushing to set the bushing in said hole in said bone.

14. The electret implant of claim 13, wherein the bushing has a screw cap to screw it inside the bushing for fixation of the electret implant in said hole in said bone, and wherein at least one screwdriver slot is made on the frontal surface of said screw cap.

15. A method for treating arthrosis, comprising:
    placing an electret implant comprising an extended body having a proximal end and a distal end into a bone, wherein a hole directed to an area of maximum destruction by pathological process is previously made in said bone, wherein said electret implant is placed with a gap into the prepared hole in said bone so that it is as close as possible to said area of maximum destruction by pathological process, wherein said implant is fixed by a fixation device by its distal end only without contact of the proximal end with the bone to prevent displacement of the implant with an optimum treatment position in the bone, wherein said electret implant is left in said bone of a patient until the time when pain syndrome appears which is connected with the fact that said electret has run down and has ceased to have stimulating effect on bone structures which leads to renewal of pathological processes which begin to grow again in said bone after the electret implant discharge and is accompanied by pain syndrome for said patient.

16. The method of claim 15, wherein when the electret runs down, the discharged implant is removed from said bone and is replaced by the charged one.

17. The method of claim 15, wherein a device for fixation of said electret implant is a bushing which is placed in said bone coaxially to said hole in said bone, and wherein said implant is placed into said hole and is removed from said hole through said bushing.

18. The method of claim 17, wherein said bushing is set aflush with the outer bone surface.

* * * * *